US00PP28755P3

(12) United States Plant Patent
Nelson et al.

(10) Patent No.: US PP28,755 P3
(45) Date of Patent: Dec. 12, 2017

(54) STRAWBERRY PLANT NAMED 'BG-6.3016'

(50) Latin Name: *Fragaria ananassa*
Varietal Denomination: BG-6.3016

(71) Applicant: Berry Genetics, Inc., Freedom, CA (US)

(72) Inventors: Steven D. Nelson, Watsonville, CA (US); Michael D. Nelson, Watsonville, CA (US); Leo W. Stoeckle, Moorpark, CA (US)

(73) Assignee: Berry Genetics, Inc., Freedom, CA (US)

( * ) Notice: Subject to any disclaimer, the term of this patent is extended or adjusted under 35 U.S.C. 154(b) by 61 days.

(21) Appl. No.: 14/756,378

(22) Filed: Sep. 4, 2015

(65) Prior Publication Data

US 2017/0071085 P1 Mar. 9, 2017

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Keith Robinson
(74) *Attorney, Agent, or Firm* — Foley & Lardner LLP

(57) ABSTRACT

This invention relates to a new and distinct variety of strawberry plant named 'BG-6.3016'. This new strawberry plant named 'BG-6.3016' is primarily adapted to the growing conditions of the central coast of California, and is primarily characterized by its fruit that tends to be longer than broad, very slight difference in shape between primary and secondary fruit, strong gloss, very firm fruit flesh, early season fruit production, and medium to long fruiting trusses.

4 Drawing Sheets

Latin name of the genus and species of the plant claimed: *Fragaria ananassa.*

Variety denomination: 'BG-6.3016'.

BACKGROUND OF THE INVENTION

The present invention relates to a new and distinct strawberry variety named 'BG-6.3016'. This new variety is a result of a controlled cross made in 2006 in an ongoing breeding program between strawberry variety designated 'BG-959' (U.S. Plant Pat. No. 17,864) and strawberry selection designated 'BG-219.068' (unpatented). Due to the combining of the reciprocal seed lots, it is unknown as to which parent variety is the seed parent and which parent variety is the pollen parent. The variety is botanically known as *Fragaria ananassa.*

The seedling resulting from the aforementioned cross was selected from a controlled breeding plot in Ventura County, Calif. in the winter of 2008. After its selection, the new variety was asexually propagated by stolons in both Siskiyou County, Calif. and San Joaquin County, Calif. The new variety was extensively tested over the next several years in fruiting fields in Ventura County, Calif. This propagation has demonstrated that the combination of traits disclosed herein as characterizing the new variety are fixed and remain true-to-type through successive generations of asexual reproduction.

BRIEF SUMMARY OF THE INVENTION

'BG-6.3016' is primarily adapted to the climate and growing conditions of the central coast of California. The nearby Pacific Ocean provides the humidity and moderate temperatures needed to produce a strong, vigorous plant and maintain fruit quality during the winter and spring production months.

The following traits have been repeatedly observed and are determined to be unique characteristics of 'BG-6.3016', which in combination distinguish this strawberry plant as a new and distinct variety:

1. Fruit that tends to be longer than broad;
2. Very slight difference in shape between primary and secondary fruit;
3. Strong gloss;
4. Very firm fruit flesh;
5. Early season fruit production; and
6. Medium to long fruiting trusses.

The strawberry variety that is believed to be most closely related to the new variety 'BG-6.3016' is 'BG-959' (U.S. Plant Pat. No. 17,864). In side-by-side comparisons to the similar strawberry variety 'BG-959', 'BG-6.3016' differs by the following combination of characteristics as described in Table 1.

TABLE 1

| Characteristic | 'BG-6.3016' | 'BG-959' (U.S. Plant Pat. No. 17,864) |
|---|---|---|
| Fruit: marketable yield (grams/plant) | 1,305 | 1,034 |
| Fruit: firmness of flesh | Very firm | Firm |
| Fruit: hollow center expression | Weak | Ranges from moderate to strong |
| Plant: size | Ranges from medium to large | Ranges from medium to small |
| Terminal leaf: shape of base | Acute | Obtuse |
| Foliage: size | Medium | Ranges from medium to small |

TABLE 1-continued

| Characteristic | 'BG-6.3016' | 'BG-959' (U.S. Plant Pat. No. 17,864) |
|---|---|---|
| Petiole: size | Ranges from medium to long | Ranges from medium to short |
| Petiole: pubescence | Sparse | Heavy |
| Flowers: position relative to foliage | Ranges from level with to above | Level with above |

For identification, a series of molecular markers have been determined for this new variety.

'BG-6.3016' differs from its parents, 'BG-959' and 'BG-219.068' by the following combination of characteristics as described in Table 2.

TABLE 2

| Characteristic | 'BG-6.3016' | 'BG-959' (U.S. Plant Pat. No. 17,864) | 'BG-219.068' |
|---|---|---|---|
| Fruit: color | Red | Red | Orange red |
| Fruit: size (gm) | 26.6 (medium) | 27.2 (medium) | 23.0 (ranges from medium to small) |
| Marketable yield (gm/plant) | 1,305 | 1,034 | 1,020 |
| Plant: size | Medium | Small | Large |

BRIEF DESCRIPTIONS OF THE PHOTOGRAPHS

The accompanying color photographs illustrate the overall appearance of typical specimens of the new strawberry variety 'BG-6.3016' at various stages of development, as true as it is reasonably possible with color reproductions of this type. Color in the photographs may differ slightly from the color value cited in the botanical descriptions which accurately describe the color of 'BG-6.3016'. The depicted plant and plant parts of the new strawberry variety 'BG-6.3016' are approximately six months old. The photographs were taken in Ventura County, Calif.

DETAILED BOTANICAL DESCRIPTION

Figure 1:
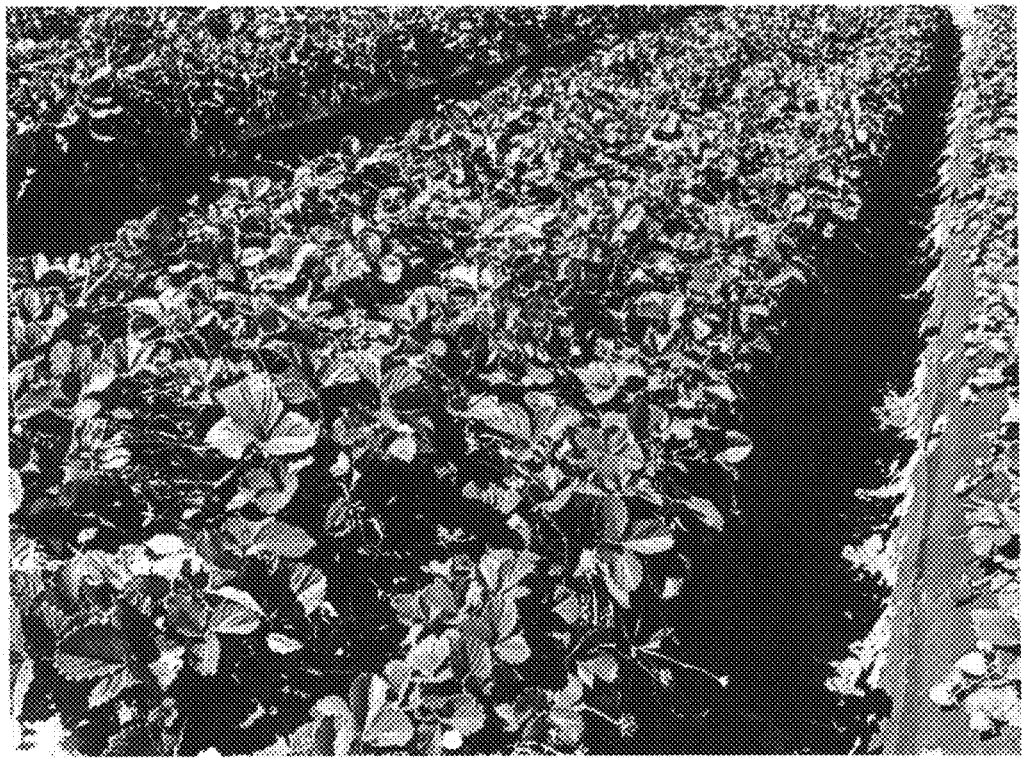
FIG. 1 shows typical fruiting field characteristics of 'BG-6.3016', taken in the month of March.
Figure 2:
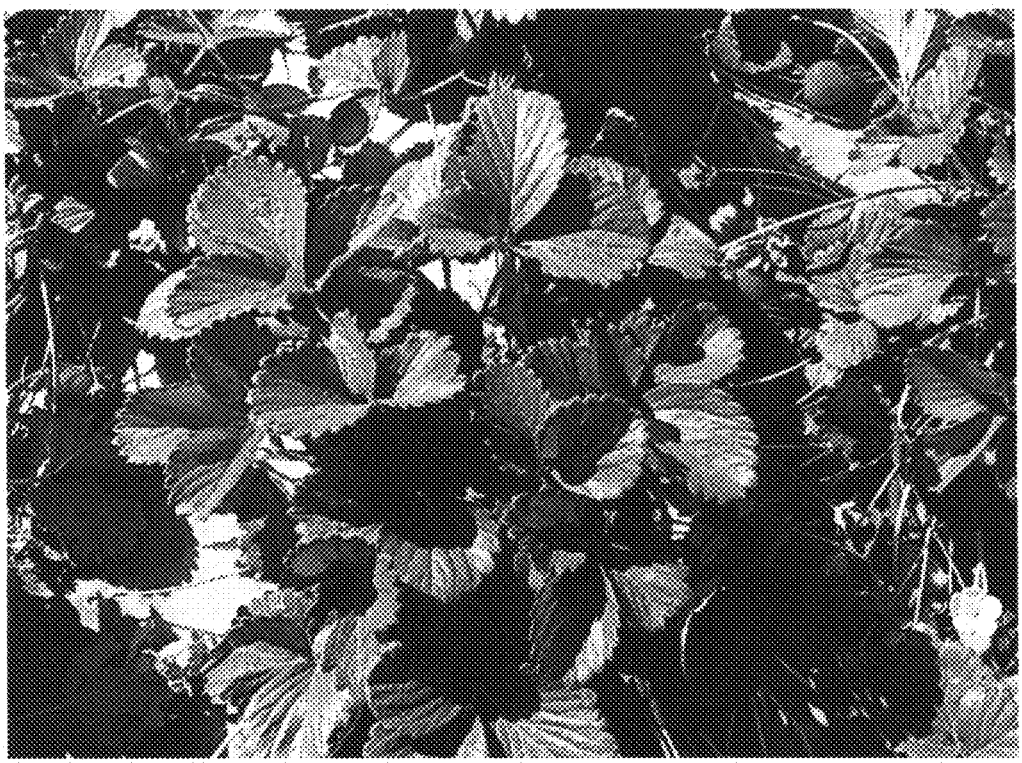
FIG. 2 shows a close-up view of the typical leaf structure of 'BG-6.3016', taken in the month of March.
Figure 3:
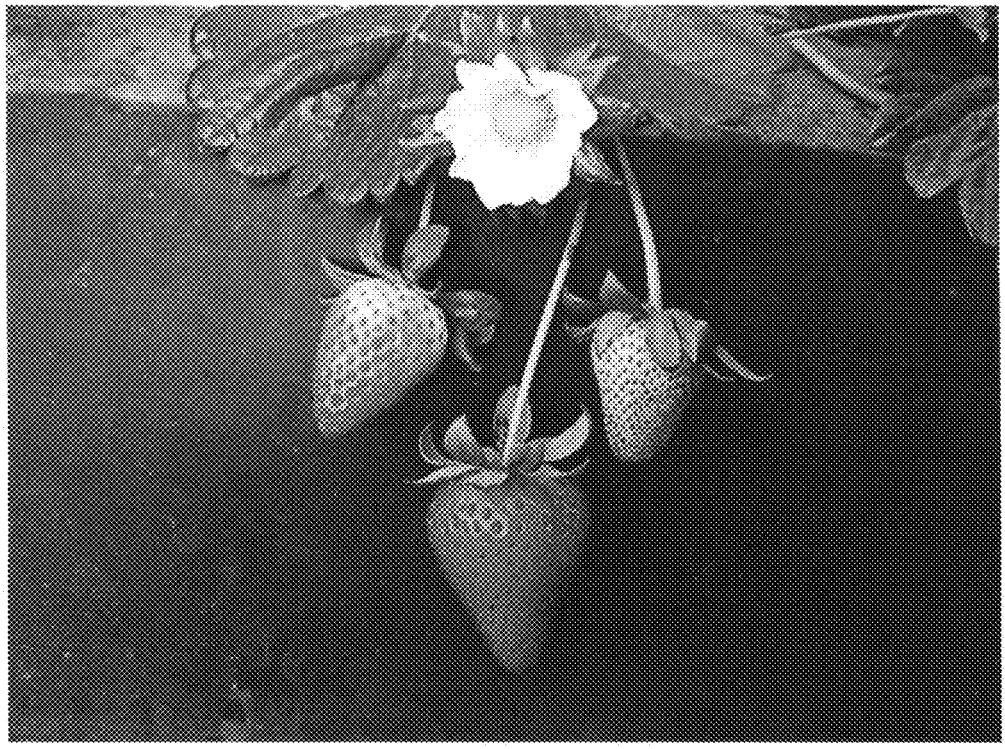
FIG. 3 shows typical mature and immature field fruit of 'BG-6.3016', taken in the month of March.
Figure 4:
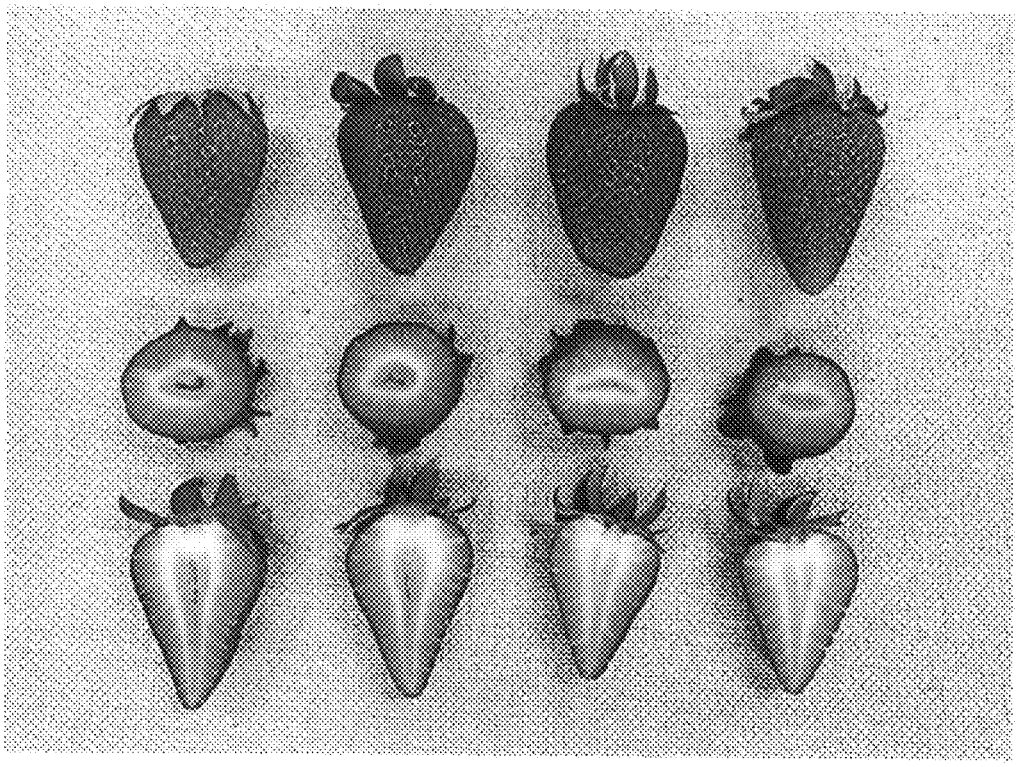
FIG. 4 shows typical internal and external mature fruit characteristics of 'BG-6.3016', taken in the month of March.

The new variety 'BG-6.3016' has not been observed under all possible environmental conditions. The characteristics of the new variety 'BG-6.3016' may vary in detail, depending upon variations in environmental factors, including weather (temperature, humidity and light intensity), day length, soil type and location. In addition, the characteristics of any parental variety or comparison variety included in Tables 1 and 2 of the present invention may vary in detail, depending upon variations in environmental factors, including weather (temperature, humidity and light intensity), day length, soil type and location.

The aforementioned photographs, together with the following description of the new variety 'BG-6.3016', unless otherwise noted, are based on observations taken during the 2015 growing season in Ventura County, Calif. These measurements and ratings were taken from plants of 'BG-6.3016' dug from a high-elevation nursery located in Siskiyou County, Calif. during early October 2014 and planted approximately four to five days later in Ventura County, Calif. The approximate age of the observed plants is six months. Yield observations including average weight and marketable yield, along with fruit quality characteristics including soluble solids, are averaged from six years of data collected from the 2010 through 2015 growing seasons. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2007).

The following characteristics describe fruit, plant, stolon, foliage, fruiting truss, flower, and pest and disease characteristics of the new strawberry 'BG-6.3016'.

Fruit characteristics:

*Color of mature fruit*.—RHS 46B (red).
*Color of internal flesh*.—RHS 45C (medium red).
*Color of core*.—RHS 39B (medium red).
*Length (cm)*.—4.7.
*Width (cm)*.—3.7.
*Size*.—Medium.
*Length/width ratio*.—1.28 (ranges from slightly longer than broad to much longer than broad).
*Calyx diameter (cm)*.—3.6.
*Season average weight (gm)*.—26.6.
*Achene color, shaded side*.—RHS 153D (yellow green group).
*Achene color, sun-exposed side*.—RHS 182A (greyed red group).
*Achene weight (mg)*.—0.58.
*Achenes per berry*.—368.
*Season marketable yield (gm/plant)*.—1,305.
*Predominant shape*.—Conical.
*Difference in shape between primary and secondary fruit*.—Slight.
*Band without achenes*.—Absent or very narrow.
*Evenness of surface*.—Even or very slightly uneven.
*Evenness of color*.—Even or very slightly uneven.
*Glossiness*.—Strong.
*Insertion of achenes*.—Level with surface.
*Position of calyx attachment*.—Inserted.
*Attitude of sepals*.—Outward.
*Size of calyx in relation to fruit diameter*.—Slightly larger.
*Adherence of calyx (when fully ripe)*.—Strong.
*Firmness of flesh*.—Ranges from firm to very firm.
*Distribution of red color of the flesh*.—Marginal and central.
*Hollow center expression*.—Weak.
*Flavor*.—Fair.
*Soluble solids (% Brix)*.—6.9.
*Time of first flowering*.—Early, November in Ventura County, Calif.
*Time of first harvest*.—Early, December in Ventura County, Calif.
*Harvest period*.—January to May.
*Harvest maturity*.—Early season.
*Type of bearing*.—Not remontant (short day).

Plant characteristics:
*Height* (*cm*).—22.2.
*Spread* (*cm*).—33.3.
*Size*.—Ranges from medium to large.
*Habit*.—Upright.
*Density*.—Ranges from sparse to medium.
*Vigor*.—Strong.
Stolon characteristics:
*Color*.—RHS 146C (yellow green group).
*Anthocyanin coloration*.—RHS 181A (greyed red group).
*Anthocyanin intensity*.—Strong.
*Pubescence*.—Medium.
*Attitude of hairs*.—Upward.
*Average quantity* (*nursery*).—Medium (ranges from 5 to 6 runners per square foot).
*Average diameter at bract* (*mm*).—3.4 (thick).
Terminal leaflet characteristics:
*Length* (*cm*).—7.5.
*Width* (*cm*).—6.7.
*Length/width ratio*.—1.12 (longer than broad).
*Shape of base*.—Acute.
*Shape of teeth*.—Obtuse (serrate to crenate).
*Serrations per leaf*.—17.7.
Foliage characteristics:
*Color of upper surface*.—RHS N137A (ranges from medium green to dark green).
*Color of underside*.—RHS 147C (yellow green group).
*Number of leaflets*.—3.
*Size*.—Medium.
*Length* (*cm*).—12.0.
*Width* (*cm*).—14.0.
*Shape in cross section*.—Slightly concave to flat.
*Interveinal blistering*.—Medium.
*Leaf glossiness*.—Ranges from medium to strong.
*Leaf variegation*.—Absent.
Petiole characteristics:
*Color*.—RHS 145A (yellow green group).
*Length* (*cm*).—16.0.
*Diameter* (*mm*).—3.4.
*Attitude of hairs*.—Upward.
*Pubescence*.—Sparse.
*Petiolule color*.—RHS 145A (yellow green group).
*Petiolule length* (*mm*).—5.3.
Stipule characteristics:
*Color*.—RHS 147C (yellow green group).
*Anthocyanin coloration*.—RHS 60B (red purple group).
*Anthocyanin intensity*.—Ranges from weak to medium.
*Length* (*mm*).—27.8.
*Width* (*mm*).—10.3.
Fruiting truss characteristics:
*Anthocyanin coloration*.—Absent.
*Anthocyanin intensity*.—Absent or very weak.
*Length at maturity* (*cm*).—29.6.
*Position relative to foliage*.—Ranges from level with to above.
*Number of flowers*.—Medium (ranges from 50 to 60 per plant season long).
*Pedicel attitude of hairs*.—Upward.
*Pubescence*.—Medium.
*Attitude at first pick*.—Prostrate.
Flower characteristics:
*Petal color*.—RHS NN155C (white group).
*Sepal color*.—RHS 137A (green group).
*Receptacle color*.—RHS 147C (yellow green group).
*Anther color*.—RHS 17A (yellow orange group).
*Corolla diameter* (*mm*).—28.0 (medium).
*Calyx diameter* (*mm*).—36.2.
*Petal length* (*mm*).—11.0.
*Petal width* (*mm*).—11.3.
*Petal length/width ratio*.—0.98 (as long as broad).
*Petals/flower*.—5.7.
*Sepal length* (*mm*).—15.8.
*Sepal width* (*mm*).—6.4.
*Sepal length/width ratio*.—2.48.
*Sepals/flower*.—11.3.
*Size of calyx relative to corolla*.—Larger.
*Size of inner calyx relative to outer calyx*.—Smaller.
*Relative position of petals* (*flowers with* 5-6 *petals*).—Ranges from touching to overlapping.
*Stamen*.—Present.
Pest and disease reactions:
*Powdery mildew* (*Sphaerotheca macularis*).—Moderate.
*Angular leaf spot* (*Xanthomonas fragaria*).—Susceptible.
*Botrytis fruit rot* (*Botrytis cinerea*).—Moderately susceptible.
*Two-spotted spider mite* (*Tetranychus urticae*).—Moderately susceptible.

We claim:

1. A new and distinct strawberry plant named 'BG-6.3016', as herein described and illustrated by the characteristics set forth above.

* * * * *